(12) United States Patent
Fox et al.

(10) Patent No.: US 11,457,892 B2
(45) Date of Patent: Oct. 4, 2022

(54) ULTRASOUND TRANSDUCER POSITIONING APPARATUS AND METHOD

(71) Applicant: Fox Components LLC, Maple Shade, NJ (US)

(72) Inventors: Anne Fox, Maple Shade, NJ (US); Jeffrey Fox, Maple Shade, NJ (US)

(*) Notice: Subject to any disclaimer, the term of this patent is extended or adjusted under 35 U.S.C. 154(b) by 114 days.

(21) Appl. No.: 17/030,725

(22) Filed: Sep. 24, 2020

(65) Prior Publication Data

US 2021/0085288 A1 Mar. 25, 2021

Related U.S. Application Data

(60) Provisional application No. 62/905,570, filed on Sep. 25, 2019.

(51) Int. Cl.
*A61B 8/00* (2006.01)
*A61B 8/08* (2006.01)

(52) U.S. Cl.
CPC .......... *A61B 8/4227* (2013.01); *A61B 8/4455* (2013.01); *A61B 8/4494* (2013.01); *A61B 8/0866* (2013.01)

(58) Field of Classification Search
None
See application file for complete search history.

(56) References Cited

U.S. PATENT DOCUMENTS

| | | | | |
|---|---|---|---|---|
| 5,191,889 A | * | 3/1993 | Mornhinweg | A61B 8/0866 600/459 |
| 7,789,836 B2 | * | 9/2010 | Van Wyk | A61B 8/4227 600/459 |
| 8,568,338 B2 | | 10/2013 | Krispi | |
| 2011/0282178 A1 | * | 11/2011 | Andersen | A61B 5/4362 600/588 |

* cited by examiner

*Primary Examiner* — Angela M Hoffa
*Assistant Examiner* — Younhee Choi
(74) *Attorney, Agent, or Firm* — Cozen O'Connor (57) ABSTRACT

An ultrasound transducer positioning apparatus and method that are capable of securing an ultrasound transducer in a desired position on a patient's body are disclosed. In some implementations, pressure exerted by the apparatus on the ultrasound transducer influences the angle at which the ultrasound energy is delivered to the patient's body.

12 Claims, 5 Drawing Sheets

ULTRASOUND TRANSDUCER POSITIONING APPARATUS AND METHOD

CROSS-REFERENCE TO RELATED APPLICATION

This application claims the benefit of U.S. provisional patent application Ser. No. 62/905,570, filed Sep. 25, 2019, the disclosure of which is hereby incorporated herein by reference in its entirety.

FIELD OF THE DISCLOSURE

Aspects of the disclosed subject matter relate generally to ultrasound monitoring techniques, and more particularly to a positioning apparatus and method that are capable of securing an ultrasound transducer in a desired position on a patient's body.

BACKGROUND

In a typical hospital delivery room, fetal monitoring is conducted via conventional ultrasound techniques. In particular, an ultrasound transducer is placed on a patient's abdomen, the ultrasonic energy penetrates the abdomen and is reflected back to the transducer, and returned energy (i.e., "echoes" received at the transducer) may be processed by the ultrasound system, enabling or facilitating a physician or nursing staff to observe or otherwise to monitor fetal heart rate, a position of the fetus, and other parameters of interest during the birthing process.

Conventional ultrasound systems may be limited by a variety of factors, however, most notable of which are the patient's weight, the patient's position, posture, or orientation during the monitoring procedure, the gestational age of the fetus, and the size and location of the fetus at a particular moment in time. Further, most conventional prior art ultrasound systems are designed for active scanning in a particular direction or orientation—i.e., if the transducer is not focusing the ultrasound energy in the right direction relative to the fetus at a particular moment in time, the transducer may not provide an accurate indication of the metrics, vital signs, or other parameters that it is intended to monitor.

In particular, false fetal heart rate interpretations may, and often do, lead to unnecessary medical interventions or other procedures prior to or during delivery, stressing both the patient and the fetus without cause. While certain medical standards recommend or suggest that fetal heart monitoring be clearly interpretable for extended or nearly continuous periods during labor and delivery, accurate positioning of the ultrasound transducer on the patient's abdomen to achieve such effective and prolonged monitoring routinely proves challenging during the birthing process. In that regard, straps are typically used to secure the ultrasound transducer to the patient's abdomen so that delivery room personnel are not constantly engaged with the ultrasound system, but these straps do not always ensure that the transducer is properly oriented.

Seasoned and clever labor and delivery nurses have learned to improvise with readily available materials to help secure the ultrasound transducer in a manner that maintains proper orientation for fetal monitoring. Wadded rags, rolls of medical tape, or other materials on hand in the delivery room may sometimes be used to assist with securing the ultrasound transducer in a correct or a desired position and orientation relative to the patient's abdomen. These improvised tools often fail to improve the targeting of ultrasonic waves as desired, however, and the medical care staff members are typically only able to employ the materials that the hospital saw fit to supply in the delivery room for other purposes.

Therefore, there is a need for an improved apparatus and method of securing an ultrasound transducer in a desired position on a patient's body. In some implementations, such an apparatus and method may be effective to control or otherwise to influence the angle at which ultrasound energy is delivered to (and received from) a patient's body.

SUMMARY OF THE DISCLOSURE

The following presents a simplified summary of the disclosure in order to provide a basic understanding of some aspects of various embodiments disclosed herein. This summary is not an extensive overview of the disclosure. It is intended neither to identify key or critical elements of the disclosed embodiments nor to delineate the scope of those embodiments. Its sole purpose is to present some concepts of the invention in a simplified form as a prelude to the more detailed description that is presented later.

The present disclosure describes an apparatus and method that facilitate securing an ultrasound transducer in a desired position on a region of a patient's body. In some implementations, an apparatus rests upon, bears on, or otherwise is made to abut against an ultrasound transducer in such a manner that, when the apparatus is cinched down to the patient, pressure exerted by the apparatus on the ultrasound transducer influences the angle at which the ultrasound energy is delivered to the patient's body. While a specific use case (i.e., fetal monitoring in connection with a delivery and birthing procedure) is discussed in detail below, it is worth noting here that the present disclosure is not intended to be limited by any particular use or application of the disclosed apparatus and method. In short, the disclosed subject matter may have utility in any of a variety of ultrasound applications involving prolonged or continuous monitoring, and during which the focus of the ultrasound energy is to be targeted by varying the angle at, and the force with, which the ultrasound transducer is urged against a portion of the patient's body.

In accordance with one implementation, for example, an ultrasound transducer positioning apparatus may generally comprise: a base having a first surface configured and operative to bear upon a selected portion of an ultrasound transducer when the ultrasound transducer is positioned on a region of a patient's body, a second surface opposite the first surface, the second surface having a transverse channel dimensioned to receive a strap to apply a force to urge the base towards the ultrasound transducer when the strap is cinched about the patient's body, and a peripheral wall extending between the first surface and the second surface; and a cap having a cap surface to engage the second surface of the base when the strap is disposed in the channel and a normal surface that extends substantially normal to the cap surface to engage the peripheral wall of the base; wherein when the cap is engaged with the base, an interference fit exerts a force on the strap disposed between the peripheral wall of the base and the normal surface of the cap to prevent movement of the strap relative to the base.

As set forth below, in accordance with the disclosed subject matter, the base may be circular, rectangular, square, oval, ovate, polygonal, or irregular in plan cross-section. Further, the base, the cap, or both, may be constructed of Teflon™, acrylic, metal (such as surgical or stainless steel), ceramics, Pyrex™ or other glass, or other medical grade or non-porous material, or a combination of these or other suitable materials.

Additionally or alternatively, the cap surface may have a transverse slot dimensioned to allow the strap to pass through the slot.

Implementations are disclosed wherein the first surface of the base is substantially planar and wherein the first surface of the base is contoured.

In accordance with another aspect of the disclosed subject matter, a method of positioning an ultrasound transducer may generally comprise: securing an ultrasound transducer to a region of a patient's body; bearing a first surface of a base of an apparatus upon a selected portion of the ultrasound transducer; employing a strap to apply a force to urge the base towards the ultrasound transducer when the strap is cinched about the patient's body; and engaging a cap with the base to create a mechanical interference fit to exert a force on the strap disposed between the cap and the base to prevent movement of the strap relative to the base.

Methods are disclosed wherein the bearing the first surface comprises providing the first surface with a circular plan cross-section, providing the first surface with a polygonal plan cross-section, and providing the first surface with an irregular plan cross-section.

Further, methods are disclosed wherein the base is constructed of a medical grade material or a non-porous material.

The foregoing and other aspects of various disclosed embodiments will be apparent through examination of the following detailed description thereof in conjunction with the accompanying drawing figures, in which like reference numerals are used to represent like components throughout, unless otherwise noted.

DETAILED DESCRIPTION

Certain aspects and features of the disclosed subject matter may be further understood with reference to the following description and the appended drawing figures. In operation, the disclosed apparatus and method may be employed in connection with any of a variety of existing ultrasound transducer embodiments. Specifically, the present disclosure provides for an apparatus that may generally urge the existing ultrasound transducer against a region of the patient's body in a desired or required manner to focus the ultrasound energy at a particular point or location.

Figure 1:
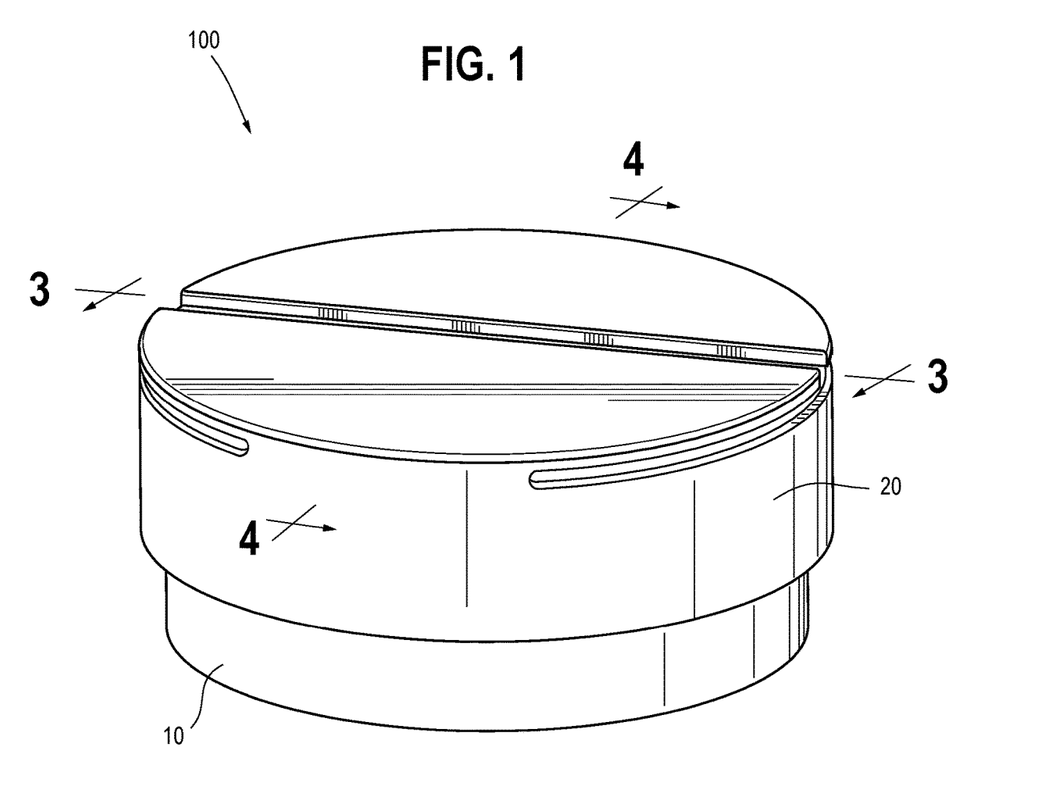
FIG. 1 is a front perspective view of one implementation of an ultrasound transducer positioning apparatus.
Figure 2:
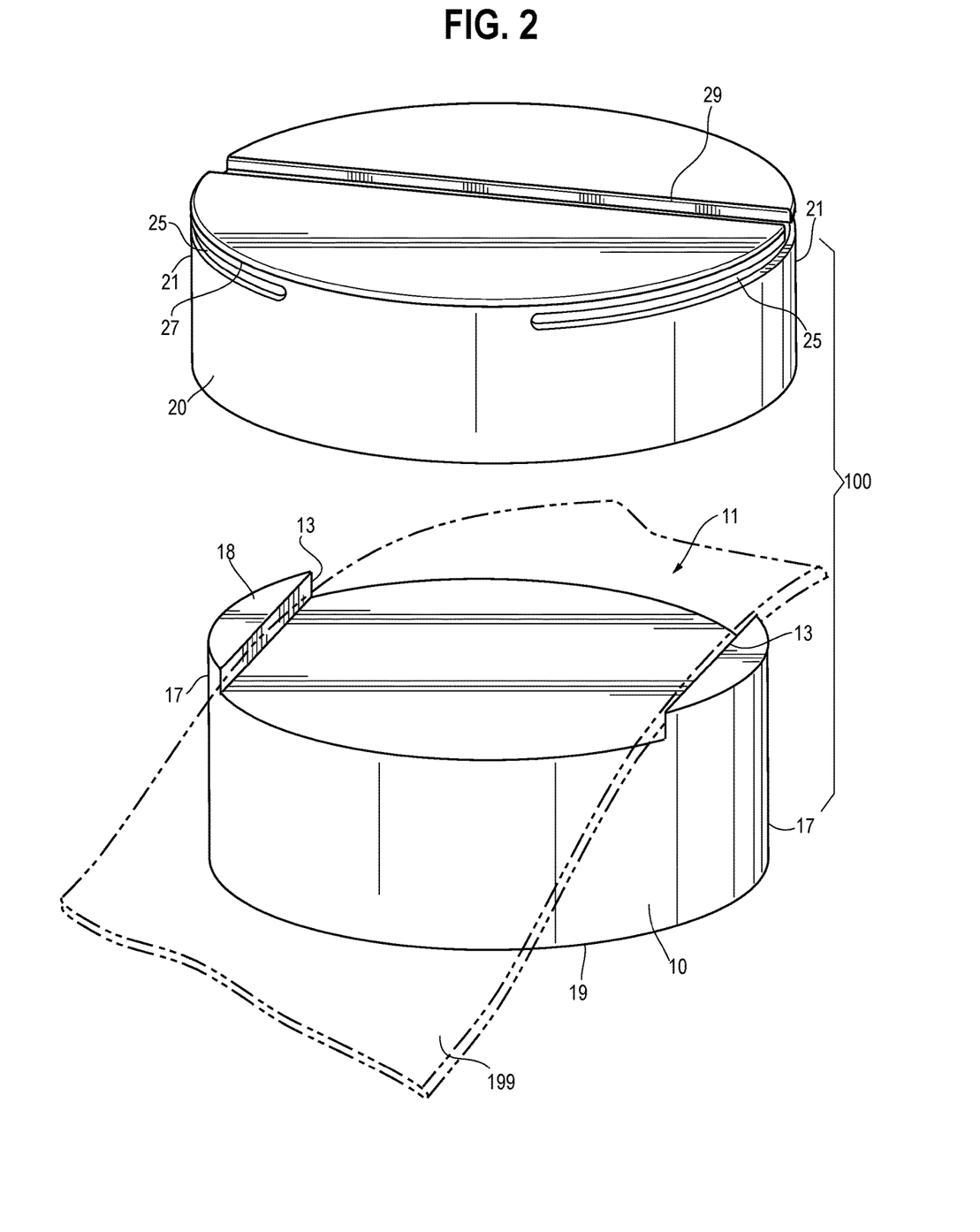
FIG. 2 is an exploded front perspective view of the ultrasound transducer positioning apparatus of FIG. 1.
Figure 3:
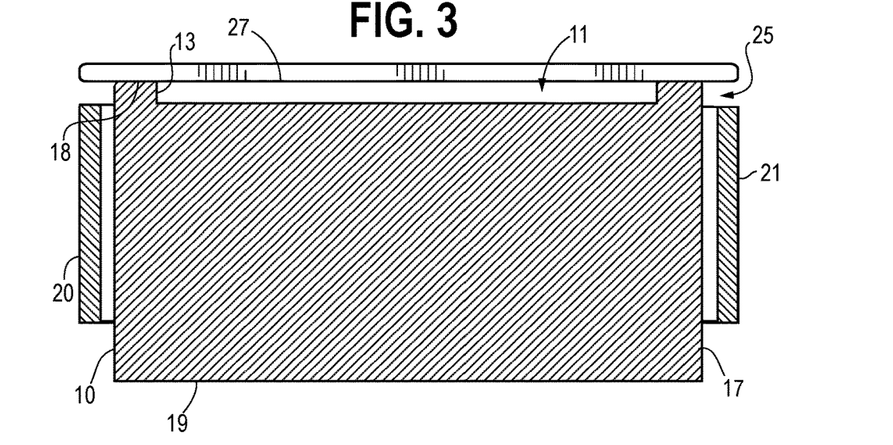
FIG. 3 is a front cross-sectional view of the ultrasound transducer positioning apparatus of FIG. 1.
Figure 4A:
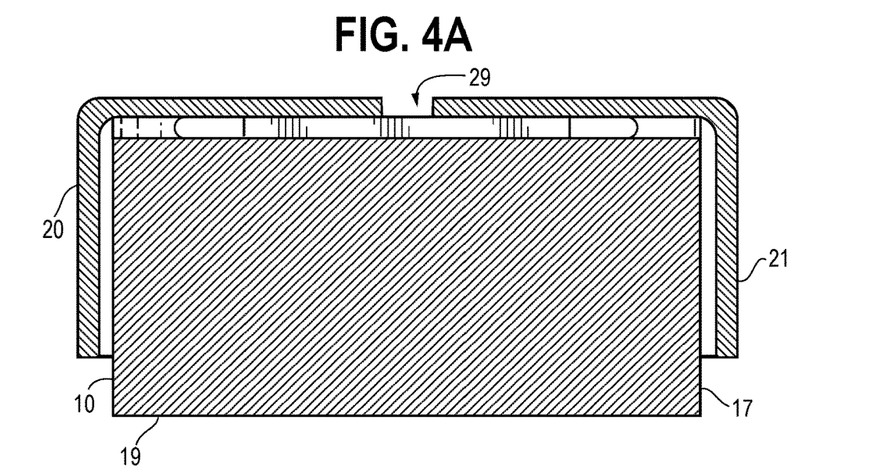
FIGS. 4A and 4B are side cross-sectional views of the ultrasound transducer positioning apparatus of FIG. 1.
Figure 4B:
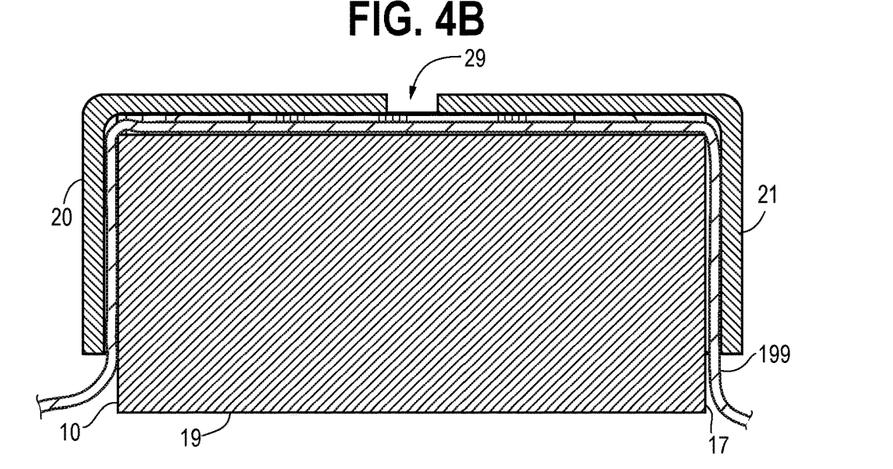

Turning now to the drawing figures, FIG. 1 is a front perspective view, and FIG. 2 is an exploded front perspective view, of one implementation of an ultrasound transducer positioning apparatus; further, FIG. 3 is a front cross-sectional view, and FIGS. 4A and 4B are side cross-sectional views, of the ultrasound transducer positioning apparatus of FIGS. 1 and 2. As illustrated, an ultrasound transducer positioning apparatus 100 may generally comprise a base 10 portion and a cover or cap 20 portion designed to engage base 10 substantially as set forth below.

More specifically, base 10 may comprise a first surface 19, a second surface 18 opposite first surface 19, a channel 11 disposed in second surface 18, and a peripheral wall 17 extending between first surface 19 and second surface 18. Cap 20 may generally comprise a cap surface 27, to engage second surface 18 of base 10 when a strap 199 is disposed in channel 11 during use, and a normal surface 21 that extends substantially normal to cap surface 27 to engage peripheral wall 17 of base 10. In use, when cap 20 is engaged with base 10, a friction fit exerts a force on strap 199 disposed between peripheral wall 17 of base 10 and normal surface 21 of cap 20 to prevent movement of strap 199 relative to base 10.

It is noted that the implementation illustrated in the drawing figures is only one example of an ultrasound transducer position apparatus, and that other shapes or configurations are contemplated. For example, while the drawing figures show apparatus 100 as having base 10 and cap 20 that are circular in plan (i.e., from a perspective looking down from above) cross-section, other shapes may be implemented as a design choice, for example, as a function of manufacturing materials and processes, cost, effective engagement with a particular type or size of ultrasound transducer with which apparatus 100 is intended to be used, or a combination of these and any of a variety of other factors. Specifically, in accordance with the disclosed subject matter, base 10 may be circular, rectangular, square, oval, ovate, polygonal, or irregular in plan cross-section; it is appreciated that cap 20 may be sized and dimensioned accordingly, to ensure snug engagement with base 10 as set forth herein.

In some polygonal or irregular plan configurations, it is noted that peripheral wall 17 may be embodied in or comprise a plurality of individual or discrete substantially planar wall segments or panels, one respective peripheral wall panel per each respective side of the polygon that forms the plan cross-section of base 10. The points at which these polygon sides (and respective peripheral wall panels) meet form angles, which may be used advantageously to apply force to an upper surface of an ultrasound transducer (reference numeral 599 in FIG. 5) as set forth below. Specifically, it will be appreciated that peripheral wall 17 need not be continuous (such as in a circular or ovate implementation), but rather may include angles (such as in a polygonal or irregular implementation) defining wall segments or panels, depending upon the plan cross-section of base 10.

Additionally, it will be appreciated that base 10, cap 20, or both, may be constructed of Teflon™, acrylic, metal (such as surgical or stainless steel), ceramics, Pyrex™ or other glass, or other medical grade or non-porous material, or a combination of these or other suitable materials. In some implementations, it may be desirable to construct (or at least to coat, glaze, sheathe, or encase) base 10 and cap 20 using non-porous or medical grade materials that may be autoclaved or otherwise sterilized for repeated use in accordance with medical facility or governmental standards, policies, regulations, or statutes. In the event that apparatus 100 is intended to be consumable or disposal (e.g., for single use applications), for instance, where sterilization is less of a concern than in reusable applications, then suitable material choices for base 10 and cap 20 may be less restricted. The present disclosure is not intended to be limited by any particular material or combination of materials used for the illustrated components, but practical applications or commercial factors may dictate material choices as a function of manufacturing parameters, cost, re-usability considerations, local, state, or federal regulations or requirements, and the like.

First surface 19 may generally be configured and operative to rest upon, bear on, or otherwise to abut against a selected portion of an upper surface of ultrasound transducer 599 when ultrasound transducer 599 is positioned on a region of a patient's body. In that regard, first surface 19 may be substantially planar (i.e., flat or two-dimensional) in a plane that is substantially normal to peripheral wall 17; alternatively, first surface 19 may be contoured or non-planar (e.g., convex or bowed away from second surface 18) to facilitate engagement with ultrasound transducer 599 in a desired or required manner. In some implementations, the construction of first surface 19 may be influenced by the plan cross-section of base 10 as a whole. For instance, where base 10 has a polygonal plan cross-section, angles in first surface 19 and peripheral wall 17 may be positioned in such a manner as to engage ultrasound transducer 599 in a particular orientation to apply desired pressure, and so first surface 19 may be substantially flat or planar; on the other hand, where base 10 has a circular or ovate plan cross-section, it may be desirable that first surface 19 is convex to assure proper engagement with an upper surface of ultrasound transducer 599 during use.

As illustrated in the drawing figures, second surface 18 may be constructed to include a transverse channel 11, which may be dimensioned to receive strap 199 to apply a force to urge base 10 towards ultrasound transducer 599 when strap 199 is cinched about the patient's body. In that regard, channel 11 may be generally defined by channel walls 13, creating a depression in second surface 18 to accommodate strap 199. Channel 11 and channel walls 13 may be sized and dimensioned to fit a particular strap 199, for instance, or they may be sized to accommodate the most popular or common type of strap that is typically employed in particular applications. For example, a typical elastic strap for use in ultrasound applications is approximately ⅛" thick and approximately 1.6" or 1.7" wide, though these dimensions will be reduced when the elastic of the strap is under tension, such as when strap 199 is used to cinch down ultrasound transducer 599 or base 10. The present disclosure is not intended to be limited by the dimensions of channel 11 or channel walls 13, as these may be selected as a design choice depending upon the nature, physical dimensions, and elastic characteristics of strap 199 with which base 10 is primarily intended to be used.

As best illustrated in FIG. 4B, strap 199 may be placed in channel 11 and cinched down to a patient (this is discussed in more detail below with reference to FIG. 5). When strap 199 is inserted in channel 11 and base 10 is positioned to urge ultrasound transducer 599 against a patient's body as desired, cap 20 may be engaged with base 10. In that regard, normal surface 21, extending substantially normal to cap surface 27, may exert a friction fit force on strap 199 such that strap 199 is secured between normal surface 21 of cap 20 and peripheral wall 17 of base 10. In this context, the term "friction fit" is intended to mean an interference fit, press fit, or other tight mechanical engagement that secures or locks strap 199 in place relative to base 10 when cap 20 is engaged over strap 199 and base 10. In operation, this friction fit prevents or minimizes movement of strap 199 relative to base 10.

Additionally or alternatively, cap 20 may include a transverse slot 29 sized and dimensioned to allow strap 199 to pass through. In the event that strap 199 is sufficiently thick, non-elastic, or incompressible that engagement of cap 20 with base 10 as illustrated in FIG. 4B is difficult or impossible, strap 199 may be fed through slot 29 in such a manner that strap 199 is only engaged by one side of normal surface 21 and peripheral wall 17—i.e., the thickness of strap 199 is only interfering between base 10 and cap 20 once, and not twice, when cap 20 is engaged with base 10, enabling the friction fit to be operative even if strap 199 is thicker than optimal. Further, this configuration (i.e., in which strap 199 is fed through slot 29) may also provide flexibility in practical applications because base 10 may be repositioned along strap 199 (such as by sliding) even in situations in which cap 20 is not entirely removed from base 10.

Similarly, cap 20 may include a horizontal slot 25, or optionally two opposing horizontal slots 25 as illustrated best in FIGS. 1, 2, and 3. Slot 25 may be sized and dimensioned to allow strap to pass through, and may be positioned to allow strap 199 selectively to be engaged by surfaces of base 10 and cap 20 such that the interference fit is adjustable to be suitable for a particular situation or application. For example, by selectively feeding strap 199 through one or both of horizontal slots 25, an ultrasound technician, care-giver, or other medical personnel may selectively adjust or tune the interference fit between normal surface 21 of cap 20 and peripheral wall 17 of base 10 (e.g., as a function of strap 199 thickness or geometry, the surfaces of cap 20 and base 10 making contact with strap 199, the linear extent of that contact, and the like). In some implementations, feeding strap 199 through one or both of horizontal slots 25 may enable base 10 to be slid or otherwise repositioned along strap 199 without requiring that cap 20 be removed from base 10; in these situations, the force exerted by the interference fit may be diminished to the point where intentionally sliding base 10 along strap 199 is possible, but may still be great enough to prevent intentional or unwanted movement of base 10 along the length of strap 199.

Figure 5:
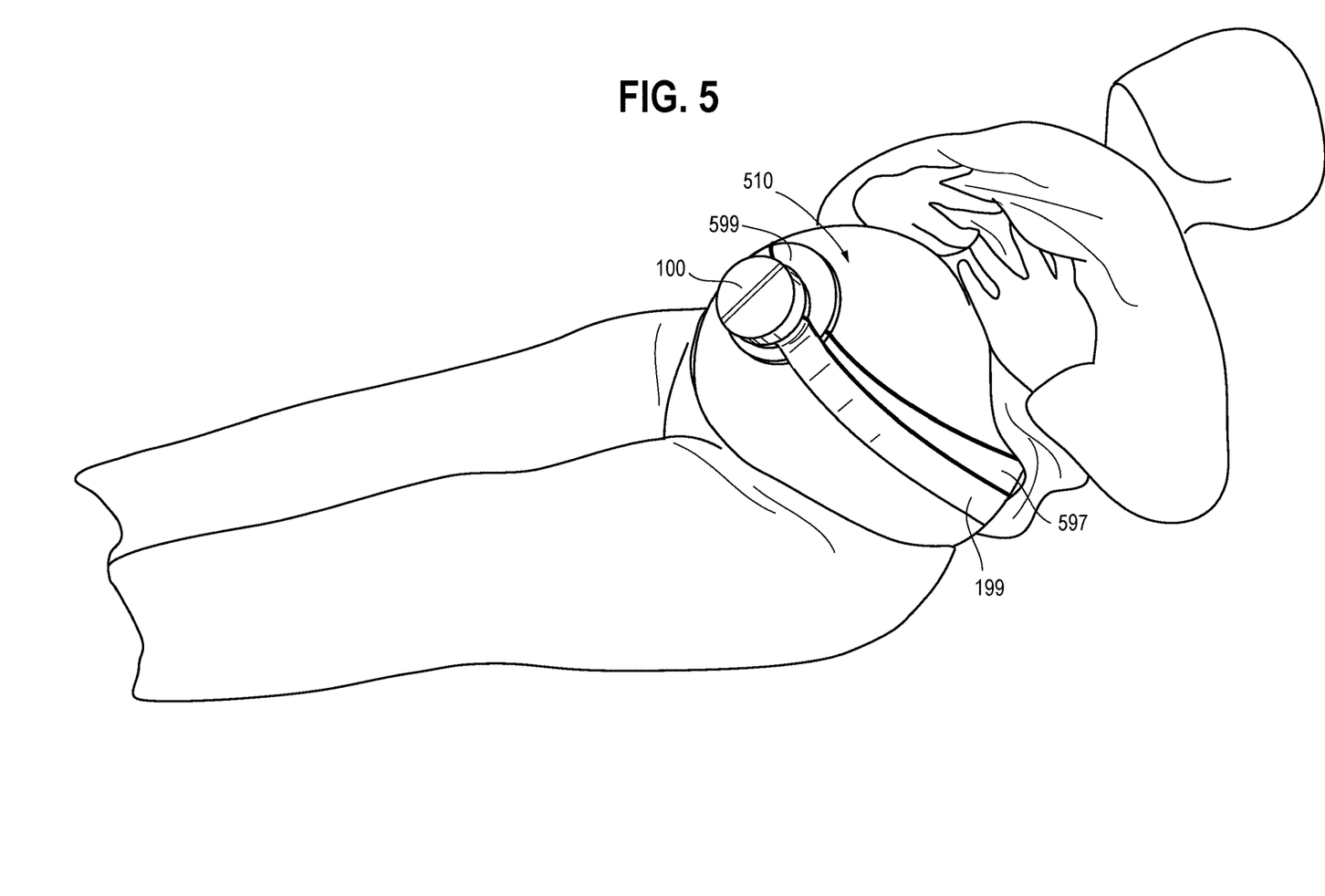
FIG. 5 is a view of the ultrasound transducer positioning apparatus of FIG. 1 in use on a patient's body.

FIG. 5 is a view of the ultrasound transducer positioning apparatus of FIG. 1 in use on a patient's body. As noted above, in use of apparatus 100, first surface 19 of base 10 is to rest upon or to bear on a selected portion of ultrasound transducer 599 when ultrasound transducer 599 is positioned on a region of a patient's body 510. In the depiction of FIG. 5, apparatus 100 is offset relative to a center of ultrasound transducer 599. By offsetting apparatus 100 relative to a center of ultrasound transducer 599, the angle at which ultrasound transducer 599 delivers ultrasonic energy to patient's body 510 may be controlled.

By way of example, in the FIG. 5 depiction, apparatus 100 is disposed low on ultrasonic transducer 599 (i.e., closer to the patient's pelvis than to the upper abdomen). In this configuration, cinching down apparatus 100 tight about body 510 will tend to urge a lower portion (i.e., closer to the pelvis) of ultrasound transducer 599 into body 510, thus angling the ultrasonic energy higher up (i.e., towards the upper abdomen). It will be appreciated that the positioning of apparatus 100 relative to the center of ultrasound transducer 599 (i.e., the direction and distance of offset), as well as the force with which apparatus 100 is cinched down to body 510, may facilitate many different outcomes, most important of which is maintaining substantially constant or continuous ultrasound contact with a fetus or other region of interest in body 510.

In this context, as those of skill in the art will appreciate, the term "cinched" is intended to mean wrapped, tightened, fastened, bound, or otherwise secured to the patient's body 510, as is typical in the ultrasound and other medical monitoring or imaging arts.

It is also noted that the manner in which apparatus 100 may be secured to patient's body 510 over ultrasound transducer 599 may be, in some practical applications, a matter of trial and error, or otherwise subject to the medical professional's skill, experience, and preference. Any of various factors mentioned above (such as the patient's weight, the patient's position, posture, or orientation during the monitoring procedure, the gestational age of the fetus, the size and location of the fetus, etc.), as well as the position, functional scan window, sensitivity, and other operational characteristics of ultrasound transducer 599, may influence the manner in which apparatus 100 is or should be deployed to achieve desired results.

Figure 6:
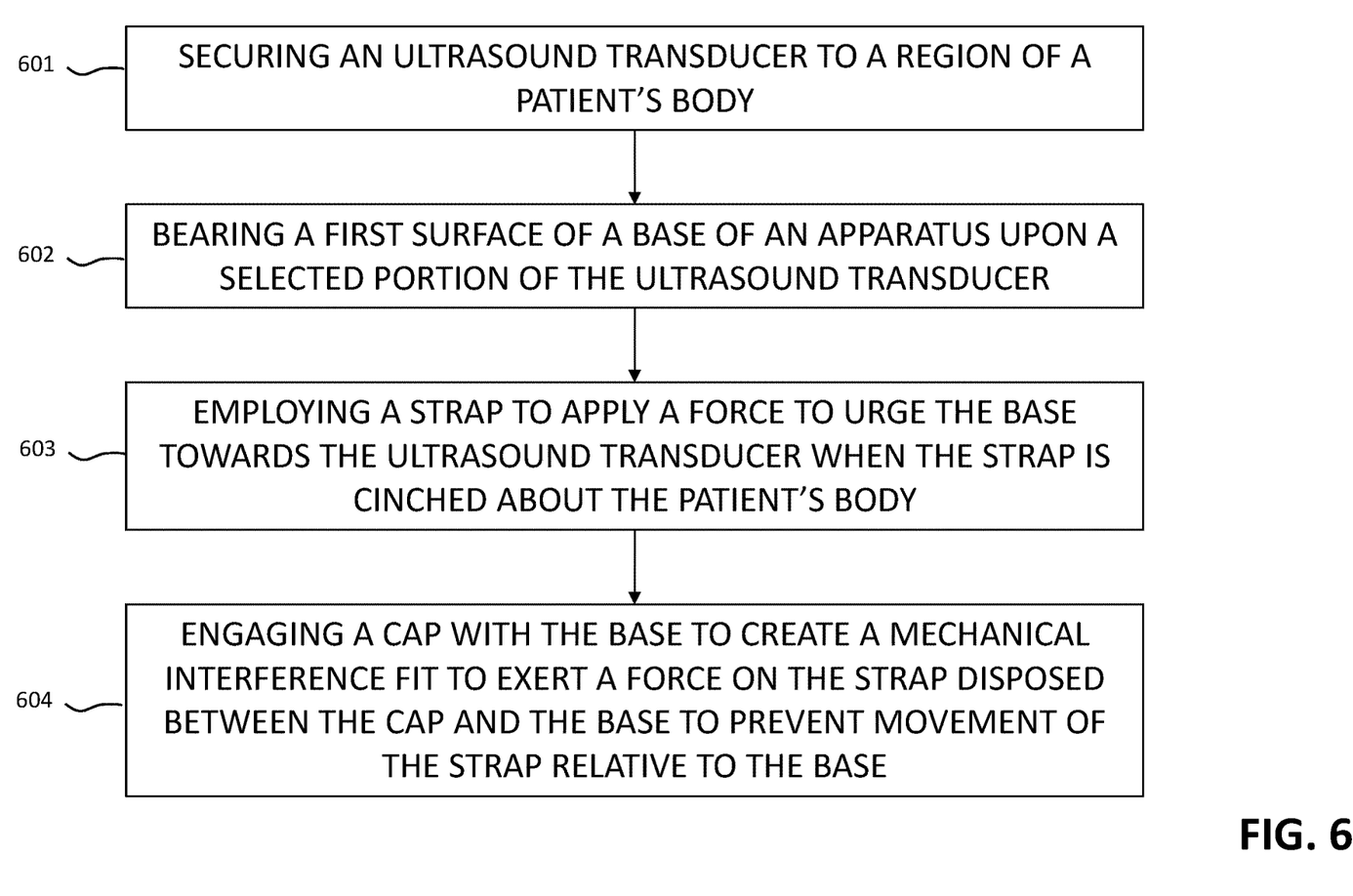
FIG. 6 is a flow diagram illustrating aspects of one embodiment of a method of positioning an ultrasound transducer on a region of a patient's body.

FIG. 6 is a flow diagram illustrating aspects of one embodiment of a method of positioning an ultrasound transducer on a region of a patient's body. In accordance with this aspect of the disclosed subject matter, a method of positioning an ultrasound transducer may generally begin by securing an ultrasound transducer (e.g., ultrasound transducer 599 in FIG. 5) to a region of a patient's body (e.g., reference numeral 510 in FIG. 5). This operation is depicted by way of example at reference numeral 601. As noted above, the operation depicted at block 601 may be executed in accordance with any of various ultrasound monitoring protocols, procedures, or regimens, and may be for fetal monitoring during labor and delivery or for other applications, as may be appropriate for ordinarily skilled artisans in the ultrasound monitoring arts. As depicted in FIG. 5, for instance, ultrasound transducer 599 may be secured to body 510 by a strap 597, though other options, such as affixing with adhesives, for instance, may be used, depending upon the nature of the ultrasound application, the preferences of the ultrasound technician or other medical staff, the equipment available at the medical facility, and the like. The present disclosure is not intended to be limited by the scope and contemplation of the ultrasound technique depicted at block 601, nor by the reasons that the ultrasound transducer is secured to the patient's body (i.e., the reasons underlying the ultrasound procedure in the first place).

The method may continue with bearing a first surface (reference numeral 19) of a base (reference numeral 10) of an apparatus (reference numeral 100) upon a selected portion of the ultrasound transducer (reference numeral 599). This operation is depicted by way of example at reference numeral 602. As noted above, placement of base 10 of apparatus 100 on ultrasonic transducer 599 may be as much an art as it is a science, and may depend upon the skill, expertise, and preferences of an ultrasound technician or other medical staff member, as well as the construction of base 10 and the force with which base 10 is applied to ultrasound transducer 599. Base 10 may be offset from ultrasound transducer 599 as set forth above, and may be placed as a function of the planarity or contour of first surface 19, of the plan cross-section of base 10, or both.

In some implementations, a method may continue by employing a strap (such as reference numeral 199) to apply a force to urge base 10 towards ultrasound transducer 599 when strap 199 is cinched about body 510. This operation is depicted by way of example at reference numeral 603. In that regard, the location (i.e., the offset, in terms of both direction and distance) of base 10 from a center of ultrasound transducer 599, as well as the force with which apparatus 100 is cinched down by strap 199, may influence, regulate, or control the direction and angle at which ultrasonic energy is delivered to body 510. This may free a nurse or other medical practitioner to engage in other important tasks rather than continually repositioning ultrasound transducer 599 during times when other care is more critical.

Finally, a method may conclude by engaging a cap (such as reference numeral 20) with the base (such as reference numeral 10) to create a mechanical interference fit to exert a force on the strap (such as reference numeral 199) disposed between the cap (such as at normal surface 27) and the base (such as at peripheral wall 17) to prevent movement of the strap relative to the base. This interference or friction fit may be a mechanical pressure fit, and may limit or otherwise restrict movement of strap 199 relative to base 10 in ordinary use.

It is noted that the arrangement of the blocks and the order of operations depicted in FIG. 6 are not intended to exclude other alternatives or options. For example, the operations depicted at blocks 602 and 603 may be iterative, or they may be made to occur substantially simultaneously in some implementations. Further, one or more of these operations may occur substantially simultaneously with the operation depicted at block 601 or 602 in instances where it is desirable to focus the ultrasonic energy in a particular location in body 510. Those of skill in the art will appreciate that the foregoing subject matter is susceptible of various design choices that may influence the order or arrangement of the operations depicted in FIG. 6.

Several features and aspects of a system and method have been illustrated and described in detail with reference to particular embodiments by way of example only, and not by way of limitation. Those of skill in the art will appreciate that alternative implementations and various modifications to the disclosed embodiments are within the scope and contemplation of the present disclosure. Therefore, it is intended that the present disclosure be considered as limited only by the scope of the appended claims.

What is claimed is:

1. An ultrasound transducer positioning apparatus comprising:
a base having a first surface configured and operative selectively to rest upon a selected portion of an ultrasound transducer when the ultrasound transducer is secured on a region of a patient's body with a first strap or adhesive, a second surface opposite the first surface, the second surface having a transverse channel dimensioned to receive a second strap to apply a first force to urge the base towards the ultrasound transducer when the second strap is cinched about the patient's body, and a peripheral wall extending between the first surface and the second surface; and
a cap having a cap surface to engage the second surface of the base when the second strap is disposed in the channel and a normal surface that extends substantially normal to the cap surface to engage the peripheral wall of the base;
wherein when the cap is engaged with the base, an interference fit exerts a second force on the second strap disposed between the peripheral wall of the base and the normal surface of the cap to prevent movement of the second strap relative to the base, and wherein when the second strap is cinched, the first force causes the first surface to orient the ultrasound transducer in such a manner as to control an angle at which ultrasonic energy is delivered to the region of the patient's body by the ultrasound transducer.

2. The apparatus of claim 1 wherein the base is circular in plan cross-section.

3. The apparatus of claim 1 wherein the base is polygonal in plan cross-section.

4. The apparatus of claim 1 wherein the base is irregular in plan cross-section.

5. The apparatus of claim 1 wherein the base is constructed of a material selected from the group consisting of acrylic, metal, ceramics, and glass.

6. The apparatus of claim 1 wherein the base is constructed of a non-porous material.

7. The apparatus of claim 1 wherein the cap surface has a transverse slot dimensioned to allow the second strap to pass through the transverse slot.

8. The apparatus of claim 1 wherein the first surface of the base is substantially planar.

9. The apparatus of claim 1 wherein the first surface of the base is contoured.

10. The apparatus of claim 1 wherein the normal surface of the cap has a first horizontal slot dimensioned to allow the second strap to pass through the first horizontal slot.

11. The apparatus of claim 10 wherein the normal surface of the cap additionally has a second horizontal slot positioned opposite the first horizontal slot and dimensioned to allow the second strap to pass through the second horizontal slot.

12. The apparatus of claim 11 wherein the first horizontal slot and the second horizontal slot enable selective adjustment of the second force on the second strap.

\* \* \* \* \*